United States Patent
Gers-Barlag et al.

[11] Patent Number: 5,914,100
[45] Date of Patent: Jun. 22, 1999

[54] WATER-RESISTANT LIGHT PROTECTION FORMULATIONS HAVING A CONTENT OF INORGANIC MICROPIGMENTS AND WATER-SOLUBLE UV FILTER SUBSTANCES

[75] Inventors: Heinrich Gers-Barlag, Kummerfeld; Anja Müller, Hamburg, both of Germany

[73] Assignee: Beiersdorf AG, Hamburg, Germany

[21] Appl. No.: 08/901,973

[22] Filed: Jul. 28, 1997

[30] Foreign Application Priority Data

Aug. 2, 1996 [DE] Germany ............... 196 31 219

[51] Int. Cl.⁶ .................. A61K 7/42; A61K 7/44
[52] U.S. Cl. .............. 424/59; 424/70.9; 424/401; 424/60; 514/937; 514/938
[58] Field of Search ............... 424/401, 59, 70.9; 514/937, 938

[56] References Cited

U.S. PATENT DOCUMENTS 5,075,102  12/1991  Hubaud et al. .................. 424/59
5,102,660   4/1992  Forestier et al. ................ 424/401
5,531,993   7/1996  Griat ............................... 424/401

*Primary Examiner*—Thurman K. Page
*Assistant Examiner*—James M. Spear
*Attorney, Agent, or Firm*—Sprung Kramer Schaefer & Briscoe

[57] ABSTRACT

Use of (a) one or more cosmetically or pharmaceutically acceptable hydrophobic inorganic pigments for achieving or increasing the water resistance of cosmetic or dermatological light protection formulations which are in the form of O/W emulsions or W/O emulsions, (b) the hydrophobic inorganic pigments being incorporated into the oily phase of the O/W emulsions or W/O emulsions, and comprise (c) one or more UV filter substances which carry one or more sulphonic acid groups or sulphonate groups on their molecular skeleton, and (d) one or more surface-active substances chosen from the group consisting of glucose derivatives and which (e) are essentially free from polyethoxylated emulsifiers.

21 Claims, No Drawings

WATER-RESISTANT LIGHT PROTECTION FORMULATIONS HAVING A CONTENT OF INORGANIC MICROPIGMENTS AND WATER-SOLUBLE UV FILTER SUBSTANCES

The present invention relates to cosmetic and dermatological light protection formulations, in particular skin-care cosmetic and dermatological light protection formulations.

The damaging effect of the ultraviolet part of solar radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or even actual burns or greater or lesser severity.

The narrower range around 308 nm is stated as the maximum erythema activity of sunlight.

Numerous compounds are known for protection against UVB radiation, these usually being derivatives of 3-benzylidenecamphor, of 4-aminobenzoic acid, of cinnamic acid, of salicylic acid, of benzophenone and also of 2-phenylbenzimidizole.

For the range between about 320 nm and about 400 nm, the so-called UVA range, it is also important to have available filter substances, since the rays thereof can also cause damage. Thus, it has been proved that UVA radiation leads to damage to the elastic and collagenic fibres of connective tissue, which makes the skin age prematurely, and that it is to be regarded as a cause of numerous phototoxic and photoallergic reactions. The damaging effect of UVB radiation can be intensified by UVA radiation.

However, UV radiation can also lead to photochemical reactions, the photochemical reaction products then intervening in skin metabolism.

Such photochemical reaction products are chiefly free-radical compounds, for example hydroxyl radicals. Undefined free-radical photoproducts which are formed in the skin itself can also show uncontrolled secondary reactions because of their high reactivity. However, singlet oxygen, a non-radical excited state of the oxygen molecule, may also occur under UV irradiation, as can short-lived epoxides and many others. Singlet oxygen, for example, is distinguished from the triplet oxygen normally present (free-radical ground state) by an increased reactivity. Nevertheless, excited, reactive (free-radical) triplet states of the oxygen molecule also exist.

UV radiation is furthermore counted among ionizing radiation. There is therefore the risk of ionic species also being formed during UV exposure, which then in turn are capable of intervening oxidatively in biochemical processes.

2-Phenylbenzimidazole-5-sulphonic acid and its salts, in particular the sodium, the potassium and the TEA salt, obtainable, for example, under the name Eusolex® 232 from Merck AG, which is distinguished by the following structural formula:

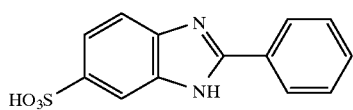

is a water-soluble UV filter substance which is advantageous per se.

Another known and advantageous but water-insoluble light protection filter substance is 4-(tert-butyl)-4'-methoxydibenzoylmethane, which is distinguished by the structure

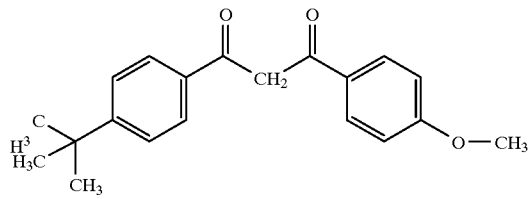

and sold by Givaudan under the brand name Parsol® 1789.

The main disadvantage of this substance is a certain instability to UV radiation, so that it is expedient also to incorporate certain UV stabilizers in formulations having a content of this substance.

Another advantageous UVB filter is tris(2-ethylhexyl) 4,4',4"-(1,3,5-triazine-2,4,6-triyltriimino)trisbenzoate, synonym: 2,4,6-tris[anilino-(p-carbo-2'-ethyl-1'-hexyloxy)]-1,3,5-triazine.

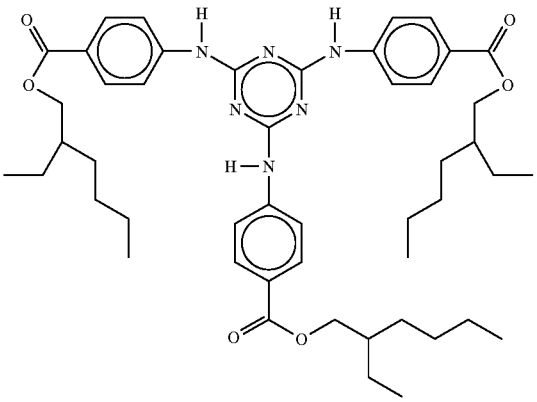

This UVB filter substance is marketed by BASF Aktiengesellschaft under the trade name UVINUL® T 150 and is distinguished by good UV absorption properties.

The main disadvantage of this UVB filter is its poor solubility in lipids. Known solvents for this UVB filter can dissolve a maximum of about 15% by weight of this filter, corresponding to about 1–1.50% by weight of dissolved, and therefore active, UV filter substance.

Another advantageous light protection filter substance is 4-methylbenzylidenecamphor, which is distinguished by the structure

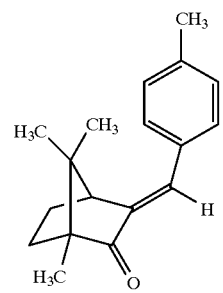

and is sold by Merck under the brand name Eusolex® 6300. These substances are distinguished by good UV filter properties per se. Yet in combination with one another or with other substances in solid form, however, their use concentration is limited.

Another advantageous light protection filter substance is 2-ethylhexyl p-methoxy-cinnamate, which is obtainable from Givaudan under the name Parsol® MCX and is distinguished by the following structure:

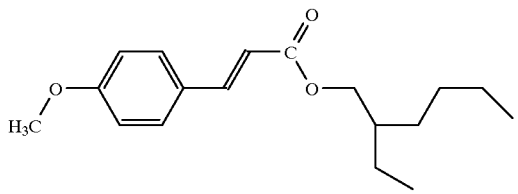

Yet another advantageous light protection filter substance is ethylhexyl 2-cyano-3,3-diphenylacrylate (octocrylene), which is obtainable from BASF under the name UVINSUL® N 539 and is distinguished by the following structure:

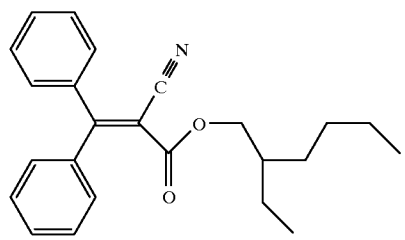

Especially if two or more of the light protection substances which are present in crystalline form under normal conditions, for example chosen from the group consisting of tris(2-ethylhexyl) 4,4',4"-(1,3,5-triazine-2,4,6-triyltriimino) trisbenzoate, 4-methylbenzylidenecamphor, 4-(tert-butyl)-4'-methoxydibenzoylmethane and titanium dioxide, are present, then according to the teaching of the prior art in each case only low use concentrations and therefore low light protection factors are possible, unless the proportion of the oily phase were to be increased disproportionately, which would, however, likewise have disadvantages.

Most of the inorganic pigments which are, as is known, used in cosmetics to protect the skin from UV rays are UV absorbers or UV reflectors. These are oxides of titanium, zinc, iron, zirconium, silicon, manganese, aluminium and cerium and mixtures thereof, as well as modifications.

The inorganic pigments are distinguished by a good light protection action per se. However, they have the disadvantage that it is difficult to incorporate them into such formulations in a satisfactory manner. Only if the particles in the final formulation are very small are they not observed as troublesome "whiting" (formation of white specks on the skin) after application to the skin. The particle sizes of such pigments are usually in the region below 100 nm. In a conventional emulsion, particles tend to a greater or lesser degree to join together to form agglomerates, which are already detectable under a light microscope. Such agglomeration it furthermore is not concluded with the preparation process of a corresponding formulation, but continues during storage. The "whiting" can therefore intensify further over a prolonged period of time. Exudation or even breaking of an emulsion can also be a medium- or long-term consequence of such agglomerations.

Another disadvantage of the use of inorganic pigments in cosmetic formulations is that in by far the majority of cases such pigments lead to severe dryness of the skin.

The disadvantage of the prior art was still that as a rule either only comparatively low light protection factors could be achieved, or that the light protection filters did not have adequate UV stability or did not have adequate physiological tolerability or did not have a sufficiently high solubility or dispersibility in cosmetic or dermatological formulations or else had other incompatibilities with cosmetic or dermatological formulations or several disadvantages at once.

Cosmetic or dermatological formulations are frequently presented as finely disperse multiphase systems in which one or more fatty or oily phases are present alongside one or more aqueous phases. The actual emulsions are, in turn, the most widespread of these systems.

In simple emulsions, one phase contains finely disperse droplets of the second phase, enclosed by an emulsifier shell (water droplets in W/O emulsions or lipid vesicles in O/W emulsions). The droplet diameters of the usual emulsions are in the range from about 1 $\mu$m to about 50 $\mu$m. Finer "macroemulsions", the droplet diameters of which are in the range of from about $10^{-1}$ $\mu$m to about 1 $\mu$m, are—without colouring additives—bluish-white in colour and opaque.

The droplet diameter of transparent or translucent microemulsions, on the other hand, is in the range from about $10^{-2}$ $\mu$m to about $10^{-1}$ $\mu$m. Such microemulsions usually have a low viscosity. The viscosity of many microemulsions of the O/W type is comparable with that of water.

A disadvantage of many O/W emulsions of the prior art is that a high content of one or more emulsifiers must always be employed, since the low droplet size causes a high interface between the phases, which as a rule must be stabilized by emulsifiers.

Water-soluble UV filter substances are electrolytes which destabilize, in particular, O/W emulsions. To counteract this destabilization, polyethoxylated emulsifiers are employed. However, these often have dermatological disadvantages, since, although the use of the customary cosmetic emulsifiers is acceptable, emulsifiers, like any chemical substance in the end, can nevertheless cause allergic reactions or reactions based on hypersensitivity of the user in an individual case.

It is thus known that certain photodermatoses are induced by certain emulsifiers, and also by various fats, and simultaneous exposure to sunlight. Such photodermatoses are also called "Mallorca acne". One object of the present invention was therefore to develop sunscreen products.

Although there are entirely advantageous cosmetic or dermatological formulations for protecting the skin from the damaging consequences of the effect of UV light, it is an often observed disadvantage that the formulations are not or not adequately water-resistant.

Light protection formulations are required and used particularly frequently on beaches and in open-air swimming pools. It is then desirable that the light protection formulation is largely water-resistant, that is to say that it is not washed off from the skin or washed off to only a small degree.

Higher light protection factors, that is to say, for example, those located above LF 15, can in general be achieved only by large amounts of UV filter substances. If a sunscreen product is also still to have a high light protection factor after bathing, the UV filter substance, in particular, must be retained on the skin.

It is already a nuisance in itself if the sunscreen product has to be applied again after bathing. During bathing itself, the use of a light protection formulation which can be washed off can even be careless and harmful to the skin under certain circumstances, since water is a poor absorber of light in the UVA and UVB range and consequently represents no noticeable UV protection, not even for submerged areas of skin.

For water-resistant light protection formulations, the prior art usually uses water-insoluble UV filter substances, water-repellent raw materials (for example silicone oils in high concentrations) and/or film-forming agents, especially high molecular weight compounds (for example PVP/hexadecene copolymers). Barriers between the UV filter substances lying on the skin and the water are built up here.

A disadvantage here is that, although diffusion of the filter substances into the water can be delayed, it cannot be prevented completely. Such products can therefore lose their protective action considerably during prolonged bathing.

The object of the present invention was thus to remedy at least some, if not all, of these disadvantages.

It was therefore surprising and unforeseeable to the expert that the use of (a) one or more cosmetically or pharmaceutically acceptable hydrophobic inorganic pigments for achieving or increasing the water resistance of cosmetic or dermatological light protection formulations which are in the form of O/W emulsions or W/O emulsions, (b) the hydrophobic inorganic pigments being incorporated into the oily phase of the O/W emulsions or W/O emulsions, and comprise (c) one or more UV filter substances which carry one or more sulphonic acid groups or sulphonate groups on their molecular skeleton, and (d) one or more surface-active substances chosen from the group consisting of glucose derivatives which are distinguished by the structural formula

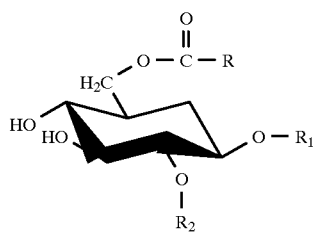

wherein R is a branched or unbranched alkyl radical having 1 to 24 carbon atoms, wherein $R_1$ is either a hydrogen atom or a branched or unbranched alkyl radical having 1 to 24 carbon atoms and wherein $R_2$ is either a hydrogen atom or a branched or unbranched acyl radical having 1 to 24 carbon atoms, and which (e) are essentially free from polyethoxylated emulsifiers, remedies the disadvantages of the prior art.

R is advantageously chosen from the group consisting of unbranched alkyl radicals, with the myristyl radical, the palmityl radical, the stearyl radical and the eicosyl radical being preferred.

$R_1$ can advantageously be a hydrogen atom, but is preferably chosen from the group consisting of methyl, ethyl, propyl and isopropyl.

$R_2$ can advantageously be a hydrogen atom, but can also advantageously be chosen from the group consisting of myristoyl, palmitoyl, stearoyl and eicosoyl.

As surface-active substances from the group consisting of glucose derivatives, methylglucose sesquistearate, which comprises approximately equal parts of the substances

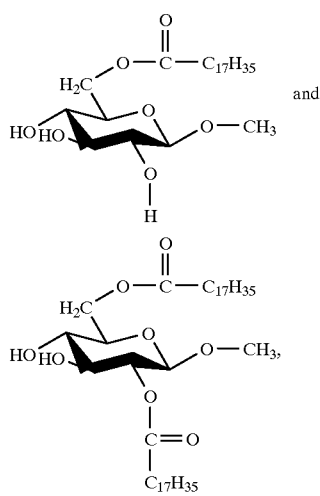

is particularly advantageously chosen. Such mixtures are commercially obtainable, for example under the trade name Tego® Care PS from the company Th. Goldschmidt KG.

According to the invention, these surface-active substances can be present in concentrations of 0.005 to 50% by weight, based on the total weight of the formulations. Concentrations of 0.5–10% by weight, in particular 1.0–5% by weight, are particularly preferred here.

Advantageous sulphonated UV filter substances in the context of the present invention are, in particular:

2-Phenylbenzimidazole-5-sulphonic acid and its salts, for example the sodium, potassium or its triethanolammonium salt:

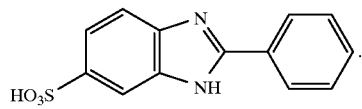

Sulphonic acid derivatives of benzophenones, preferably 2-hydroxy-4-methoxybenzophenone-5-sulphonic acid and its salts, for example the corresponding sodium, potassium or triethanolammonium salt:

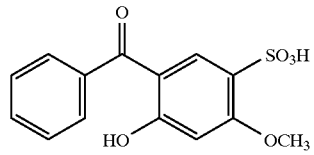

Sulphonic acid derivatives of 3-benzylidenecamphor, such as, for example, 4-(2-oxo- 3-bornylidene-methyl) benzenesulphonic acid and its salts, for example the corresponding sodium, potassium or triethanolammonium salt:

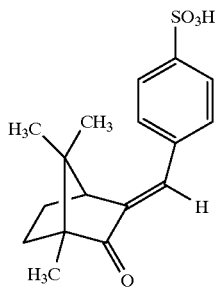

2-Methyl-5-(2-oxo-3-bornylidenemethyl)benzenesulphonic acid and its salts, for example the corresponding sodium, potassium or triethanolammonium salt:

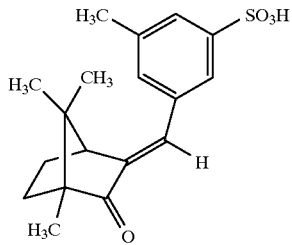

1,4-di(2-oxo-10-sulpho-3-bornylidenemethyl)-benzene and its salts (the corresponding 10-sulphato compounds, for example the corresponding sodium, potassium or triethanolammonium salt), also called benzene-1,4-di(2-oxo-3-bornylidenemethyl-10-sulphonic acid):

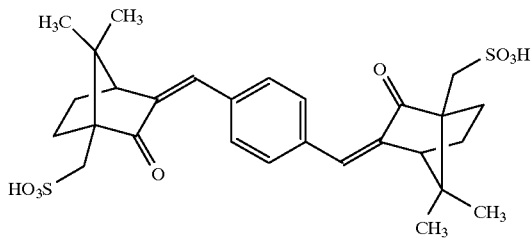

Phenylene-1,4-bis(2-benzimidazyl)-3,3', 5,5'-tetrasulphonic acid:

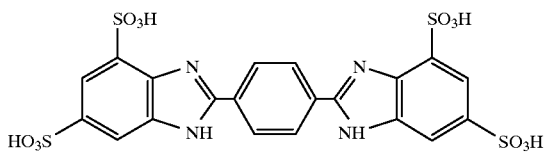

and its salts, for example the corresponding sodium, potassium or triethanolammonium salt, in particular phenylene-1,4-bis-(2-benzimidazyl)-3,3', 5,5'-tetrasulphonic acid bis-sodium salt:

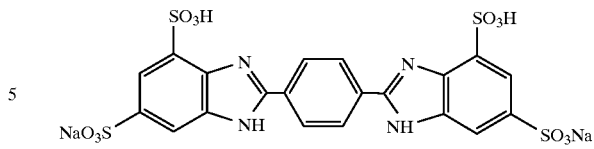

Such formulations remedy the disadvantages described for the prior art in a surprising manner. Higher light protection factors can be achieved according to the invention than could have been assumed from the prior art.

Furthermore, it could not be foreseen from the prior art that water-resistant formulations which can achieve a considerably higher water resistance than formulations of the prior art, with which high light protection factors can also still be achieved, for example, after bathing, are obtainable according to the invention.

Cosmetic and dermatological formulations according to the invention comprise inorganic pigments based on metal oxides and/or other metal compounds which are sparingly soluble or insoluble in water, in particular the oxides of titanium ($TiO_2$), zinc (ZnO), iron (for example $Fe_2O_3$), zirconium ($ZrO_2$), silicon ($SiO_2$), manganese (for example MnO), aluminium ($Al_2O_3$) and cerium (for example $Ce_2O_3$), mixed oxides of the corresponding metals and mixtures of such oxides. The pigments are particularly preferably pigments based on $TiO_2$.

The inorganic pigments are present according to the invention in hydrophobic form, i.e. they have been given a water repellent treatment on the surface. This surface treatment can comprise providing the pigment with a thin hydrophobic layer by processes known per se.

Such a process comprises, for example, producing the hydrophobic surface layer by a reaction in accordance with n $TiO_2$+m $(RO)_3Si$—$R'$→n $TiO_2$ (surface).

n and m here are stoichiometric parameters to be employed as desired, and R and R' are the desired organic radicals. Hydrophobized pigments prepared, for example, analogously to DE-A 33 14 742 are of advantage.

Advantageous $TiO_2$ pigments are obtainable, for example, under the trade names T 805 from Degussa or MT 100 T from Tayca or M 160 from Kemira.

Those products which are obtainable under the trade name Tioveil® from Tioxide, for example, can be chosen as water-dispersible (that is to say hydrophilic) inorganic micropigments which are additionally present, if desired.

The total amount of inorganic pigments, in particular hydrophobic inorganic micropigments, in the finished cosmetic or dermatological formulations is advantageously chosen from the range of 0.1–30% by weight, preferably 0.1–10.0, in particular 0.5–6.0% by weight, based on the total weight of the formulations.

In the cosmetic or dermatological formulations according to the invention, the more sparingly soluble components furthermore also have a better solubility than in the formulations of the prior art, even if several such components are present.

According to the invention, the agglomeration of inorganic pigment particles (which of course are present in dispersed and not dissolved form) with the consequences of "whiting", exudation or breaking of the emulsion, can furthermore be prevented, even if one or more components which are more sparingly soluble are present.

Light protection formulations which have a higher stability, in particular stability to decomposition under the influence of light, especially UV light, than could have been expected from the prior art are furthermore obtainable according to the invention. In particular, the stability of 4-(tert-butyl)-4'-methoxydibenzoylmethane is increased drastically.

Formulations which have a particularly good skin tolerance, it being possible for valuable constituents to be distributed particularly readily on the skin, are furthermore obtainable according to the invention.

It is possible according to the invention to substantially increase the amounts of tris(2-ethylhexyl) 4,4',4"-(1,3,5-triazine-2,4,6-triyltriimino)tris-benzoate employed, and also those of the other light protection filter substances present as a solid under normal conditions, in cosmetic or dermatological formulations compared with the prior art.

It was furthermore astonishing that stabilization of solutions of tris(2-ethylhexyl) 4,4',4"-(1,3,5-triazine-2,4,6-triyltriimino)trisbenzoate is effected according to the invention, since the latter substance not only has a poor solubility but also readily recrystallizes from its solution again.

The total amount of water-soluble UV filter substance or substances in the finished cosmetic or dermatological formulations is advantageously chosen from the range of 0.1–10.0% by weight, preferably 0.5–6.0% by weight, based on the total weight of the formulations.

The total amount of 2-phenylbenzimidazole-5-sulphonic acid (if it is this substance which is to be employed as a sulphonated UV filter substance in the context of the present invention) or salts thereof in the finished cosmetic or dermatological formulations is advantageously chosen from the range of 0.1–10.0% by weight, preferably 0.5–6.0% by weight, based on the total weight of the formulations.

The total amount of 2-hydroxy-4-methoxybenzophenone-5-sulphonic acid (if it is this substance which is to be employed as a sulphonated UV filter substance in the context of the present invention) or salts thereof in the finished cosmetic or dermatological formulations is advantageously chosen from the range of 0.1–10.0% by weight, preferably 0.5–6.0% by weight, based on the total weight of the formulations.

The total amount of 4-(2-oxo-3-bornylidenemethyl) benzenesulphonic acid (if it is this substance which is to be employed as a sulphonated UV filter substance in the context of the present invention) or salts thereof in the finished cosmetic or dermatological formulations is advantageously chosen from the range of 0.1–10.0% by weight, preferably 0.5–6.0% by weight, based on the total weight of the formulations.

The total amount of 2-methyl-5-(2-oxo-3-bornylidenemethyl)benzenesulphonic acid (if it is this substance which is to be employed as a sulphonated UV filter substance in the context of the present invention) or salts thereof in the finished cosmetic or dermatological formulations is advantageously chosen from the range of 0.1–10.0% by weight, preferably 0.5–6.0% by weight, based on the total weight of the formulations.

The total amount of benzene-1,4-di(2-oxo-3-bornylidenemethyl-10-sulphonic acid) (if it is this substance which is to be employed as a sulphonated UV filter substance in the context of the present invention) or salts thereof in the finished cosmetic or dermatological formulations is advantageously chosen from the range of 0.1–10.0% by weight, preferably 0.5–6.0% by weight, based on the total weight of the formulations.

The total amount of phenylene-1,4-bis(2-benzimidazyl)-3,3',5,5'-tetrasulphonic acid (if it is this substance which is to be employed as a sulphonated UV filter substance in the context of the present invention) or salts thereof in the finished cosmetic or dermatological formulations is advantageously chosen from the range of 0.1–10.0% by weight, preferably 0.5–6.0% by weight, based on the total weight of the formulations.

The total amount of tris(2-ethylhexyl) 4,4',4"-(1,3,5-triazine-2,4,6-triyltriimino)trisbenzoate (as an additional UV filter substance which is optionally to be employed per se) in the finished cosmetic or dermatological formulations is advantageously chosen from the range of 0.1–10.0% by weight, preferably 0.5–6.0% by weight, based on the total weight of the formulations.

The total amount of 4-(tert-butyl)-4'-methoxydibenzoylmethane (as an additional UV filter substance which is optionally to be employed per se) in the finished cosmetic or dermatological formulations is advantageously chosen from the range of 0.1–10.0% by weight, preferably 0.5–6.0% by weight, based on the total weight of the formulations.

The total amount of 4-methylbenzylidenecamphor (as an additional UV filter substance which is optionally to be employed per se) in the finished cosmetic or dermatological formulations is advantageously chosen from the range of 0.1–10.0% by weight, preferably 0.5–6.0% by weight, based on the total weight of the formulations.

The total amount of 2-ethylhexyl p-methoxy-cinnamate (as an additional UV filter substance which is optionally to be employed per se) in the finished cosmetic or dermatological formulations is advantageously chosen from the range of 0.1–15.0% by weight, preferably 0.5–7.5% by weight, based on the total weight of the formulations.

The total amount of ethylhexyl 2-cyano-3,3-diphenylacrylate (as an additional UV filter substance which is optionally to be employed per se) in the finished cosmetic or dermatological formulations is advantageously chosen from the range of 0.1–15.0% by weight, preferably 0.5–10.0% by weight, based on the total weight of the formulations.

It is furthermore advantageous to combine the active compound combinations according to the invention with further UVA and/or UVB filters.

It may furthermore be advantageous, where appropriate, to combine the active compound combinations according to the invention with further UVA and/or UVB filters, for example certain salicylic acid derivatives, such as

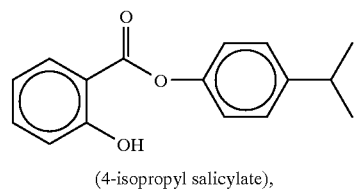

(4-isopropyl salicylate),

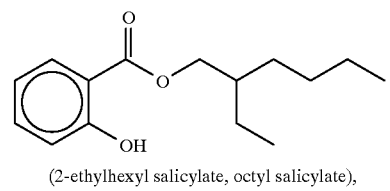

(2-ethylhexyl salicylate, octyl salicylate),

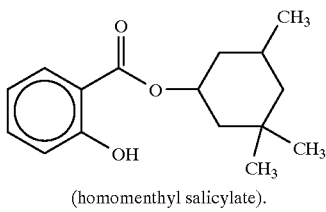

(homomenthyl salicylate).

The total amount of one or more salicylic acid derivatives in the finished cosmetic or dermatological formulations is advantageously chosen from the range of 0.1–15.0% by weight, preferably 0.5–8.0% by weight, based on the total weight of the formulations. If ethylhexyl salicylate is chosen, it is advantageous to choose the total amount thereof from the range of 0.1–5.0% by weight, preferably 0.5–2.5% by weight. If homomenthyl salicylate is chosen, it is advantageous to choose the total amount thereof from the range of 0.1–10.0% by weight, preferably 0.5–5.0% by weight.

It may also be advantageous to combine the combinations according to the invention with UVA filters which have usually been contained to date in cosmetic formulations. These substances are preferably derivatives of dibenzoylmethane, in particular 1-( 4'-tert-butyl-phenyl)-3-(4'-methoxyphenyl)propane-1,3-dione and 1-phenyl-3-(4'-isopropylphenyl)propane-1,3-dione. The invention also relates to these combinations and to formulations which comprise these combinations. The amounts used for the UVB combinations can be employed.

It is advantageous according to the invention to employ further UVA filters and/or UVB filters, in addition to the combinations according to the invention, the total amount of filter substances being, for example, 0.1% by weight to 30% by weight, preferably 0.5 to 10% by weight, in particular 1 to 6% by weight, based on the total weight of the formulations, in order to provide cosmetic formulations which protect the skin from the entire range of ultraviolet radiation. They can also serve as sunscreen compositions.

Advantageous oil-soluble UVB filter substances are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)benzoate and amyl 4-(dimethylamino)benzoate;

esters of cinnamic acid, preferably 2-ethylhexyl 4-methoxycinnamate and isopentyl 4-methoxycinnamate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzalmalonate;

2,4,6-trianilino-(p-carbo-2'-ethyl-1'-hexyloxy)-1,3,5-triazine.

The list of UVB filters mentioned which can be used in combination with the active compound combinations according to the invention is of course not intended to be limiting.

As mentioned above, the present invention allows a comparable or even higher light protection filter action to be achieved than was allowed to date by the prior art, with a lower total concentration of UV filter substances. It has also proved to be particularly advantageous to introduce an additional content of cosmetically or pharmaceutically acceptable electrolytes. Over wide concentration ranges, it is possible for the concentration of the UV filter substance or substances to be reduced by the same or certainly at least a comparable content as that with which the recipe is topped up, as it were, with one or more electrolytes. A total content of about 0.5% by weight of UV filter substances has as a rule proved to be the lower limit at which this behaviour manifests itself in a relevant manner to the consumer.

The formulations according to the invention therefore advantageously comprise electrolytes, in particular one or more salts with the following anions: chlorides, and furthermore inorganic oxo element anions, and of these in particular sulphates, carbonates, phosphates, borates and aluminates. Electrolytes based on organic anions can also advantageously be used, for example lactates, acetates, benzoates, propionates, tartrates, citrates and many others. Comparable effects are also to be achieved by ethylenediaminetetraacetic acid and salts thereof.

Ammonium, alkylammonium, alkali metal, alkaline earth metal, magnesium, iron and zinc ions are preferably used as cations of the salts. It requires no mention per se that only physiologically acceptable electrolytes should be used in cosmetics. Potassium chloride, sodium chloride, magnesium sulphate, zinc sulphate and mixtures thereof are particularly preferred. Salt mixtures such as occur in the natural salt from the Dead Sea are also advantageous.

The concentration of the electrolyte or electrolytes should be about 0.1–10.0% by weight, particularly advantageously about 0.3–8.0% by weight, based on the total weight of the formulation.

The cosmetic and/or dermatological light protection formulations according to the invention can have the customary composition and be used for cosmetic and/or dermatological light protection, and furthermore for treatment, care and cleansing of the skin and/or hair and as a make-up product in decorative cosmetics.

For use, the cosmetic and dermatological formulations according to the invention are applied to the skin and/or hair in an adequate amount in the manner customary for cosmetics.

Those cosmetic and dermatological formulations which are in the form of a sunscreen composition are particularly preferred. These can additionally comprise at least one further UVA filter and/or at least one further UVB filter.

The cosmetic and dermatological formulations according to the invention can comprise cosmetic auxiliaries such as are usually used in such formulations, for example preservatives, bactericides, perfumes, dyestuffs, pigments which have a colouring action, thickeners, humidifying and/or humectant substances, fats, oils, waxes or other customary constituents of a cosmetic or dermatological formulation, such as alcohols, polyols, polymers, foam stabilizers, electrolytes, organic solvents, further emulsifiers or silicone derivatives.

It may be advantageous, for example, to choose the additional emulsifier or emulsifiers from the group consisting of surface-active substances chosen from the group consisting of glycerol mono- and dicarboxylic acid monoesters of the general formula

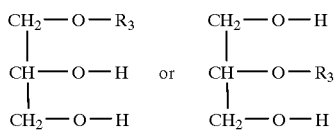

wherein $R_3$ is a branched or unbranched acyl radical having 6–24 carbon atoms.

An additional content of antioxidants is in general preferred. Favourable antioxidants which can be used according to the invention are all the antioxidants which are suitable or customary for cosmetic and/or dermatological applications.

The antioxidants are advantageously chosen from the group consisting of amino acids (for example glycine, histidine, tyrosine and tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, chlorogenic acid and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homo-cysteine-sulphoximine, buthionine sulphones and penta-, hexa- and heptathionine-sulphoximine) in very low tolerated dosages (for example pmol to μmol/kg), and furthermore (metal) chelators (for example α-hydroxy-fatty acids, palmitic acid, phytic acid and lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example γ-linolenic acid, linoleic acid and oleic acid), folic acid and derivatives thereof, ubiquinone and ubiquinol and derivatives thereof, vitamin C and derivatives (for example ascorbyl palmitate, Mg ascorbyl phosphate and ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO and $ZnSO_4$), selenium and derivatives thereof (for example selenium-methionine), stilbene and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

The amount of the abovementioned antioxidants (one or more compounds) in the formulations is preferably 0.001 to 30% by weight, particularly preferably 0.05–20% by weight, in particular 1–10% by weight, based on the total weight of the formulation.

If vitamin E and/or derivatives thereof are the antioxidant or antioxidants, it is advantageous to choose the particular concentrations thereof from the range of 0.001–10% by weight, based on the total weight of the formulation.

If vitamin A or vitamin A derivatives or carotenes or derivatives thereof are the antioxidant or antioxidants, it is advantageous to choose the particular concentrations thereof from the range of 0.001–10% by weight, based on the total weight of the formulation.

The oily phase of the formulations according to the invention is advantageously chosen from the group consisting of esters of saturated and/or unsaturated, branched and/or unbranched alkanecarboxylic acids of chain length 3 to 30 C atoms and saturated and/or unsaturated, branched and/or unbranched alcohols of chain length 3 to 30 C atoms, or from the group consisting of esters of aromatic carboxylic acids and saturated and/or unsaturated branched and/or unbranched alcohols of chain length 3 to 30 C atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and naturally occurring mixtures of such esters, for example jojoba oil.

The oily phase can furthermore advantageously be chosen from the group consisting of branched and unbranched hydrocarbons and waxes, silicone oils, dialkyl ethers, the group consisting of saturated or unsaturated, branched or unbranched alcohols, and fatty acid triglycerides, that is to say the triglycerol esters of saturated and/or unsaturated, branched and/or unbranched alkanecarboxylic acids having a chain length of 8 to 24, in particular 12–18 C atoms. The fatty acid triglycerides can advantageously be chosen, for example, from the group consisting of synthetic, semi-synthetic and naturally occurring oils, for example olive oil, sunflower oil, soya oil, groundnut oil, rapeseed oil, almond oil, palm oil, coconut oil, palm kernel oil and many others.

Any desired mixtures of such oil and wax components are also advantageously to be employed in the context of the present invention.

The oily phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicaprylyl ether.

Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous.

Of the hydrocarbons, paraffin oil, squalane and squalene are advantageously to be used in the context of the present invention.

The oily phase can furthermore have a content of cyclic or linear silicone oils or consist entirely of such oils, although it is preferable to use an additional content of ether oily phase components in addition to the silicone oil or silicone oils.

Cyclomethicone (octamethylcyclotetrasiloxane) is advantageously employed as a silicone oil to be used according to the invention. However, other silicone oils are also advantageously to be used in the context of the present invention, for example hexamethylcyclotrisiloxane, polydimethylsiloxane or poly(methylphenylsiloxane).

Mixtures of cyclomethicone and isotridecyl isononanoate and of cyclomethicone and 2-ethylhexyl isostearate are furthermore particularly advantageous.

The content of the oily phase is advantageously between 1 and 50% by weight, based on the total weight of the formulations, preferably 2.5–30% by weight, particularly preferably 5–15% by weight.

The aqueous phase of the formulations according to the invention optionally advantageously comprises alcohols, diols or polyols of low C number, as well as ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the group consisting of the so-called Carbopols, for example Carbopols of types 980, 981, 1382, 2984 and 5984, in each case individually or in combination.

The following examples are intended to illustrate the present invention without limiting it. Unless stated otherwise, all the amounts data, contents and percentage contents are based on the weight and the total amount or on the total weight of the formulations.

EXAMPLE 1

|  | % by weight |
| --- | --- |
| Methylglucose sesquistearate | 5.00 |
| Caprylic/capric triglyceride | 5.00 |
| Octyldodecanol | 5.00 |
| Dicaprylyl ether | 2.00 |
| Phenylbenzimidazolesulphonic acid | 4.00 |
| TiO$_2$ (hydrophobic) | 3.00 |
| Glycerol | 3.00 |
| Tocopheryl acetate | 1.00 |
| NaOH | q.s. |
| Perfume, preservative | q.s |
| Water | to 100.00 |

EXAMPLE 2

|  | % by weight |
| --- | --- |
| Methylglucose sesquistearate | 5.00 |
| Caprylic/capric triglyceride | 1.67 |
| Octyldodecanol | 1.67 |
| Dicaprylyl ether | 1.67 |
| Phenylbenzimidazolesulphonic acid | 4.00 |
| TiO$_2$ (hydrophobic) | 5.00 |
| TiO$_2$ (hydrophilic) | 5.00 |
| Butylene glycol | 3.00 |
| Tocopheryl acetate | 1.00 |
| NaOH | q.s. |
| Perfume, preservative | q.s. |
| Water | to 100.00 |

EXAMPLE 3

|  | % by weight |
| --- | --- |
| Methylglucose sesquistearate | 3.00 |
| Caprylic/capric triglyceride | 5.00 |
| Octyldodecanol | 5.00 |

-continued

|  | % by weight |
| --- | --- |
| Dicaprylyl ether | 1.67 |
| Benzene-1,4-di(2-oxo-3-bornylidene-methyl-10-sulphonic acid) | 4.00 |
| TiO$_2$ (hydrophobic) | 5.00 |
| Glycerol monostearate | 2.00 |
| Glycerol | 3.00 |
| Tocopheryl acetate | 1.00 |
| NaOH | q.s. |
| Perfume, preservative | q.s. |
| Water | to 100.00 |

EXAMPLE 4

|  | % by weight |
| --- | --- |
| Methylglucose sesquistearate | 5.00 |
| Caprylic/capric triglyceride | 1.67 |
| Octyldodecanol | 1.67 |
| C$_{12-15}$-Alkyl benzoates | 5.00 |
| Phenylbenzimidazolesulphonic acid | 2.00 |
| TiO$_2$ (hydrophobic) | 2.50 |
| Tris [anilino(p-carbo-2'-ethyl-1'-hexyloxy)]triazine | 3.00 |
| 4-(tert-Butyl)-4'-methoxydibenzoyl-methane | 2.00 |
| Butylene glycol | 3.00 |
| 4-Methyl-benzylidenecamphor | 2.00 |
| Tocopheryl acetate | 1.00 |
| NaOH | q.s. |
| Perfume, preservative | q.s. |
| Water | to 100.00 |

We claim:

1. A cosmetic or dermatologic formulation in the form of an O/W emulsion or W/O emulsion comprising an oily phase comprising the following ingredients:

a) one or more cosmetically or pharmaceutically acceptable hydrophobic inorganic pigments;

b) one or more UV filter substances which comprise one or more sulphonic acid groups or sulphonate groups as a part of their molecular skeleton; and c) one or more surface-active substances selected from the group consisting of glucose derivatives of the structural formula:

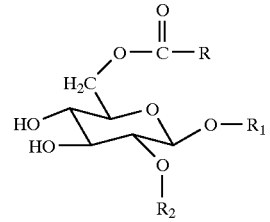

in which R is a branched or unbranched alkyl radical having 1 to 24 carbon atoms, R$_1$ is a hydrogen atom or a branched or unbranched alkyl radical having 1 to 24 carbon atoms, and R$_2$ is a hydrogen atom or a branched or unbranched acyl radical having 1 to 24 carbon atoms; and d) being essentially free from polyethoxylated emulsifiers.

2. A cosmetic or dermatologic formulation according to claim 1, wherein in the structural formula of ingredient c), R is selected from the group consisting of myristyl, palmityl, stearyl and eicosyl; R₁ is selected from the group consisting of hydrogen, methyl, ethyl, propyl and isopropyl; and/or R₂ is selected from the group consisting of hydrogen, myristoyl, palmitoyl, stearoyl and eicosoyl.

3. A cosmetic or dermatologic formulation according to claim 1, wherein ingredient c) comprises methylglucose sesquistearate.

4. A cosmetic or dermatologic formulation according to claim 1, wherein ingredient b) comprises a water-soluble, cosmetically or pharmaceutically acceptable UV filter substance or substances.

5. A cosmetic or dermatologic formulation according to claim 4, wherein the water-soluble, cosmetically or pharmaceutically acceptable UV filter substance or substances are selected from the group consisting of 2-phenylbenzimidazole-5-sulphonic acid and salts thereof, the sulphonic acid derivatives of benzophenones, the sulphonic acid derivatives of 3-benzylidenecamphor, 2-methyl-5-(2-oxo-3-bornylidenemethyl)benzenesulphonic acid and salts thereof, and 1,4-di(2-oxo-10-sulpho-3-bornylidenemethyl)benzene and salts thereof.

6. A cosmetic or dermatologic formulation according to claim 5, wherein the water-soluble, cosmetically or pharmaceutically acceptable UV filter substance or substances are selected from the group consisting of 2-phenylbenzimidazole-5-sulphonic acid and salts thereof, 2-hydroxy-4-methoxybenzophenone-5-sulphonic acid and salts thereof, 4-(2-oxo-3-bornylidenemethyl)benzenesulphonic acid and salts thereof, 2-methyl-5-(2-oxo-3-bornylidenemethyl)benzenesulphonic acid and salts thereof, and 1,4-di(2-oxo-10-sulpho-3-bornylidenemethyl)benzene and salts thereof.

7. A cosmetic or dermatologic formulation according to claim 6, wherein the water-soluble, cosmetically or pharmaceutically acceptable UV filter substance or substances are selected from the group consisting of 2-phenylbenzimidazole-5-sulphonic acid and salts thereof, 2-hydroxy-4-methoxybenzophenone-5-sulphonic acid and salts thereof, 4-(2-oxo-3-bornylidenemethyl)benzenesulphonic acid and the sodium, potassium or triethanolammonium salts thereof, 2-methyl-5-(2-oxo-3-bornylidenemethyl)benzenesulphonic acid and the sodium, potassium or triethanolammonium salts thereof, and 1,4-di(2-oxo-10-sulpho-3-bornylidenemethyl)benzene and salts thereof.

8. A method for achieving or increasing the water resistance of a cosmetic or dermatologic formulation for protecting skin from the damaging effects of UV light, said cosmetic or dermatologic formulation being one according to claim 1 in the form of a O/W emulsion or W/O emulsion, said method comprising incorporating into an oily phase of said emulsion the following ingredients:

a) one or more cosmetically or pharmaceutically acceptable hydrophobic inorganic pigments;

b) one or more UV filter substances which comprise one or more sulphonic acid groups or sulphonate groups as a part of their molecular skeleton; and c) one or more surface-active substances selected from the group consisting of glucose derivatives of the structural formula:

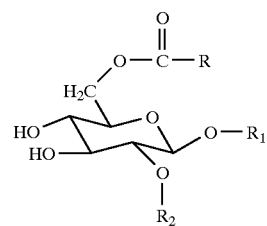

in which R is a branched or unbranched alkyl radical having 1 to 24 carbon atoms, R₁ is a hydrogen atom or a branched or unbranched alkyl radical having 1 to 24 carbon atoms, and R₂ is a hydrogen atom or a branched or unbranched acyl radical having 1 to 24 carbon atoms;

said emulsion being essentially free from polyethoxylated emulsifiers.

9. A method according to claim 8, wherein in the structural formula of ingredient c), R is selected from the group consisting of myristyl, palmityl, stearyl and eicosyl; R₁ is selected from the group consisting of hydrogen, methyl, ethyl, propyl and isopropyl; and/or R₂ is selected from the group consisting of hydrogen, myristoyl, palmitoyl, stearoyl and eicosoyl.

10. A method according to claim 8, wherein ingredient c) comprises methylglucose sesquistearate.

11. A method according to claim 8, wherein ingredient b) comprises a water-soluble, cosmetically or pharmaceutically acceptable UV filter substance or substances.

12. A method according to claim 11, wherein the water-soluble, cosmetically or pharmaceutically acceptable UV filter substance or substances are selected from the group consisting of 2-phenylbenzimidazole-5-sulphonic acid and salts thereof, the sulphonic acid derivatives of benzophenones, the sulphonic acid derivatives of 3-benzylidenecamphor, 2-methyl-5-(2-oxo-3-bornylidenemethyl)benzenesulphonic acid and salts thereof, and 1,4-di(2-oxo-10-sulpho-3-bornylidenemethyl)benzene and salts thereof.

13. A method according to claim 12, wherein the water-soluble, cosmetically or pharmaceutically acceptable UV filter substance or substances are selected from the group consisting of 2-phenylbenzimidazole-5-sulphonic acid and salts thereof, 2-hydroxy-4-methoxybenzophenone-5-sulphonic acid and salts thereof, 4-(2-oxo-3-bornylidenemethyl)benzenesulphonic acid and salts thereof, 2-methyl-5-(2-oxo-3-bornylidenemethyl)benzenesulphonic acid and salts thereof, and 1,4-di(2-oxo-10-sulpho-3-bornylidenemethyl)benzene and salts thereof.

14. A method according to claim 13, wherein the water-soluble, cosmetically or pharmaceutically acceptable UV filter substance or substances are selected from the group consisting of 2-phenylbenzimidazole-5-sulphonic acid and salts thereof, 2-hydroxy-4-methoxybenzophenone-5-sulphonic acid and salts thereof, 4-(2-oxo-3-bornylidenemethyl)benzenesulphonic acid and the sodium, potassium or triethanolammonium salts thereof, 2-methyl-5-(2-oxo-3-bornylidenemethyl)benzenesulphonic acid and the sodium, potassium or triethanolammonium salts thereof, and 1,4-di(2-oxo-10-sulpho-3-bornylidenemethyl)benzene and salts thereof.

15. A method of protecting skin from the damaging effects of UV light comprising applying to skin a UV light protective effective amount of a cosmetic or dermatologic formulation according to claim 1 in the form of an O/W emulsion or W/O emulsion comprising an oily phase comprising the following ingredients:
- a) one or more cosmetically or pharmaceutically acceptable hydrophobic inorganic pigments;
- b) one or more UV filter substances which comprise one or more sulphonic acid groups or sulphonate groups as a part of their molecular skeleton; and
- c) one or more surface-active substances selected from the group consisting of glucose derivatives of the structural formula:

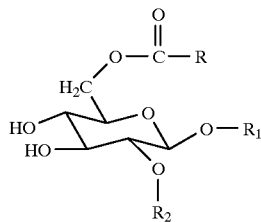

in which R is a branched or unbranched alkyl radical having 1 to 24 carbon atoms, $R_1$ is a hydrogen atom or a branched or unbranched alkyl radical having 1 to 24 carbon atoms, and $R_2$ is a hydrogen atom or a branched or unbranched acyl radical having 1 to 24 carbon atoms; and
- d) being essentially free from polyethoxylated emulsifiers.

16. A method according to claim 15, wherein in the structural formula of ingredient c), R is selected from the group consisting of myristyl, palmityl, stearyl and eicosyl; $R_1$ is selected from the group consisting of hydrogen, methyl, ethyl, propyl and isopropyl; and/or $R_2$ is selected from the group consisting of hydrogen, myristoyl, palmitoyl, stearoyl and eicosoyl.

17. A method according to claim 15, wherein ingredient c) comprises methylglucose sesquistearate.

18. A method according to claim 15, wherein ingredient b) comprises a water-soluble, cosmetically or pharmaceutically acceptable UV filter substance or substances.

19. A method according to claim 18, wherein the water-soluble, cosmetically or pharmaceutically acceptable UV filter substance or substances are selected from the group consisting of 2-phenylbenzimidazole-5-sulphonic acid and salts thereof, the sulphonic acid derivatives of benzophenones, the sulphonic acid derivatives of 3-benzylidenecamphor, 2-methyl-5-(2-oxo-3-bornylidenemethyl)benzenesulphonic acid and salts thereof, and 1,4-di(2-oxo-10-sulpho-3-bornylidenemethyl)benzene and salts thereof.

20. A method according to claim 19, wherein the water-soluble, cosmetically or pharmaceutically acceptable UV filter substance or substances are selected from the group consisting of 2-phenylbenzimidazole-5-sulphonic acid and salts thereof, 2-hydroxy-4-methoxybenzophenone-5-sulphonic acid and salts thereof, 4-(2-oxo-3-bornylidenemethyl)benzenesulphonic acid and salts thereof, 2-methyl-5-(2-oxo-3-bornylidenemethyl)benzenesulphonic acid and salts thereof, and 1,4-di(2-oxo-10-sulpho-3-bornylidenemethyl)benzene and salts thereof.

21. A method according to claim 20, wherein the water-soluble, cosmetically or pharmaceutically acceptable UV filter substance or substances are selected from the group consisting of 2-phenylbenzimidazole-5-sulphonic acid and salts thereof, 2-hydroxy-4-methoxybenzophenone-5-sulphonic acid and salts thereof, 4-(2-oxo-3-bornylidenemethyl)benzenesulphonic acid and the sodium, potassium or triethanolammonium salts thereof, 2-methyl-5-(2-oxo-3-bornylidenemethyl)benzenesulphonic acid and the sodium, potassium or triethanolammonium salts thereof, and 1,4-di(2-oxo-10-sulpho-3-bornylidenemethyl)benzene and salts thereof.

* * * * *